United States Patent [19]

Main et al.

[11] 4,143,140

[45] Mar. 6, 1979

[54] MORPHOLINE CARBOXAMIDES AND USE THEREOF

[75] Inventors: Brian G. Main; Jeffrey J. Barlow, both of Macclesfield, England

[73] Assignee: Imperial Chemical Industries Limited, London, England

[21] Appl. No.: 908,458

[22] Filed: May 22, 1978

[30] Foreign Application Priority Data

May 23, 1977 [GB] United Kingdom ............... 21608/77

[51] Int. Cl.² ................. C07D 295/18; A61K 31/535; A61K 31/165; C07C 127/19
[52] U.S. Cl. ............................... 424/248.54; 424/322; 544/168; 260/553 A
[58] Field of Search ............................. 544/168, 169; 424/248.54

[56] References Cited

FOREIGN PATENT DOCUMENTS 1455116 10/1976 United Kingdom ..................... 260/553

*Primary Examiner*—Natalie Trousof
*Assistant Examiner*—R. W. Ramsuer
*Attorney, Agent, or Firm*—Cushman, Darby & Cushman

[57] ABSTRACT

1-Hydroxyphenoxy-3-ureidoethylamino-2-propanol derivatives, processes for their manufacture, pharmaceutical compositions containing them and methods of using them in the treatment of heart failure. The compounds possess cardio-selective β-adrenergic stimulant activity. Representative of the compounds disclosed is 1-p-hydroxyphenoxy-3-β-(morpholinocarbonamido)ethylamino-2-propanol.

8 Claims, No Drawings

MORPHOLINE CARBOXAMIDES AND USE THEREOF

This invention relates to cardiac stimulants and more particularly it relates to novel alkanolamine derivatives which possess said property.

In United Kingdom Pat. No. 1,455,116 there are described and claimed inter alia alkanolamine derivatives of the formula:

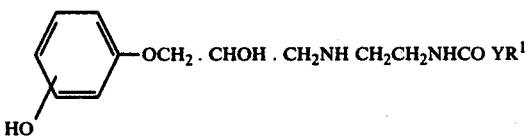

wherein Y may be an imino, alkylimino, iminoalkylene or iminoalkyleneoxy radical and $R^1$ may be hydrogen or a hydrocarbon radical such as an alkyl, alkenyl, cycloalkyl or aryl radical. These compounds are stated to have, in addition to β-adrenergic blocking activity, substantial cardiac stimulant activity. This definition does not include within its scope compounds wherein Y is a disubstituted imino radical and the substituent $R^1$ is an aliphatic substituent in which the total group $-YR^1$ contains an oxygen atom.

It is believed that an ideal cardiac stimulant should produce in a dog with cardiac reflexes removed an increase in heart rate of about one half of the increase produced under similar conditions by isoprenaline, preferably between 45% and 60% of that produced by isoprenaline; that it should exert this heart-rate-increasing effect at a low oral dose; and that at said low oral dose it should be substantially devoid of the blood-pressure-lowering effect which is exerted by isoprenaline at a corresponding dose. No compound specifically exemplified in United Kingdom Specification No. 1,455,116 has exactly this balance of properties, which are hereinafter referred to as cardio-selective β-ardrenergic stimulant properties, although many compounds described in said specification do indeed possess substantial cardiac stimulant properties.

We have now found, and herein lies our invention, that certain compounds which are closely related to the compounds described in said specification, but which are outside the scope of the claims thereof, do possess the desired balance of cardioselective β-adrenergic stimulant properties.

According to the invention there is provided an alkanolamine derivative of the formula:

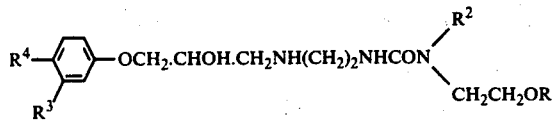

wherein $R^3$ and $R^4$, which may be the same or different, each is hydrogen or a hydroxy radical, provided that at least one of $R^3$ and $R^4$ is a hydroxy radical, and wherein either R is hydrogen, methyl or ethyl and $R^2$ is methyl, ethyl or a radical of the formula $-CH_2CH_2OR$, wherein R has the meaning stated above, or R and $R^2$ are joined together to form the ethylene ($-CH_2CH_2-$) radical; or an acid-addition salt thereof.

It will be observed that the alkanolamine derivative of the invention possesses an asymmetric carbon atom, namely the carbon atom of the $-CHOH-$ group in the alkanolamine side-chain, and it can therefore exist in racemic and optically-active forms. It is to be understood that this invention encompasses the racemic form of the alkanolamine derivative and any optically-active form which possesses β-adrenergic stimulant activity, it being a matter of common general knowledge how a racemic compound may be resolved into optically-active forms, and how the β-adrenergic stimulant activity of these forms may be determined. It is further to be understood that β-adrenergic stimulant activity usually predominates in that optically-active form which has the "S" absolute configuration of the said $-CHOH-$ group.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, fumarate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

Specific alkanolamine derivatives of the invention are those hereinafter described in the Examples. Of these, a preferred compound is 1-(p-hydroxyphenoxy)-3-β-(morpholino-carbonamido) ethylamino-2-propanol, especially the S-(−)-isomer thereof or an acid-addition salt thereof.

The alkanolamine derivative of the invention may be manufactured by any chemical process known to be useful for the manufacture of chemically-analogous compounds, and in particular may be manufactured by any of the processes described for the manufacture of similar compounds in United Kingdom Pat. No. 1,455,116.

According to a further feature of the invention there is provided a process for the manufacture of the alkanolamine derivative of the invention which comprises assembling in sequence, by chemical methods publically-known for such purpose, the six radicals:

(i) an aryloxy radical of the formula:

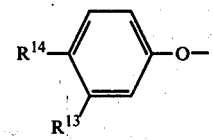

wherein $R^{13}$ and $R^{14}$, which may be the same or different, each stands for hydrogen or for a radical of the formula $R^5O-$ wherein $R^5$ stands for hydrogen or for a protecting group, provided that at least one of $R^{13}$ and $R^{14}$ is a radical of the formula $R^5O-$;

(ii) a radical of the formula:

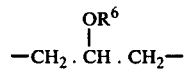

wherein $R^6$ stands for hydrogen or for a protecting group;

(iii) a radical of the formula $-NR^7-$, wherein $R^7$ stands for hydrogen or for a protecting group;

(iv) a radical of the formula —CH$_2$CH$_2$NR$^8$— wherein R$^8$ stands for hydrogen or for a protecting group;

(v) a carbonyl (—CO—) radical; and (vi) a radical of the formula

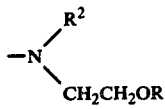

wherein R and R$^2$ have the meanings stated above; whereafter if one or more of R$^5$, R$^6$, R$^7$ and R$^8$ stands for a protecting group the one or more protecting groups are removed.

The various stages of the assembly may be carried out in any possible order, and in particular any of the sequences of reactions described in United Kingdom Pat. No. 1,455,116 may be applied to the synthesis of the alkanolamine derivatives of the present invention. The protecting groups R$^6$, R$^7$ and R$^8$ may be similar to the corresponding protecting groups described in said specification, and R$^5$ when a protecting group is preferably the benzyl radical.

One preferred process for the manufacture of the alkanolamine derivative of the invention comprises the reaction of a compound of the formula:

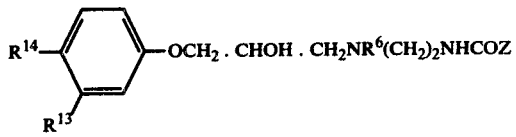

wherein R$^6$, R$^{13}$ and R$^{14}$ have the meanings stated above and wherein Z stands for a displaceable radical, with an amine of the formula:

HNR$^2$—CH$_2$CH$_2$OR wherein R and R$^2$ have the meanings stated above, followed by removal of any protecting group present. R$^6$ is preferably the benzyl radical and one or both of R$^{13}$ and R$^{14}$ is preferably the benzyloxy radical, the benzyl radicals being removed by hydrogenolysis.

A second preferred process for the manufacture of the alkanolamine derivative of the invention comprises the reaction of a compound of the formula:

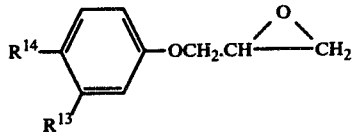

wherein R$^{13}$ and R$^{14}$ have the meanings stated above, with a compound of the formula:

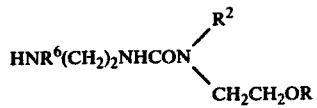

wherein R, R$^2$ and R$^6$ have the meanings stated above, followed by the removal of any protecting group present. R$^6$ is preferably hydrogen and one or both of R$^{13}$ and R$^{14}$ is preferably the benzyloxy radical, the benzyl part of this being removed of hydrogenolysis. Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (—)-O,O-di-p-toluoyltartaric acid or (—)-2, 3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses β-adrenergic stimulant activity, and furthermore this activity is cardioselective. The activity may be demonstrated by the increase in heart rate produced by administration of the compound to a dog, pretreated with syrosingopine to remove catecholamines, in which the vagal nerves have been cut in order to isolate the heart, and the absence of decrease in blood pressure in a denervated hind limb of the same dog when the limb is perfused at constant volume blood flow. Unlike isoprenaline, a known cardiac stimulating agent which is not cardioselective, a preferred alkanolamine derivative of the invention or a salt thereof is well absorbed when administered orally and has a substantial duration of action. At doses of an alkanolamine derivative of the invention which produce effective cardiac stimulation in dogs, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; α-adrenergic blocking agents, for example phentolamine and sympathomimetic bronchodilators, for example isoprenaline, orciprenaline, adrenaline and ephedrine.

When used for the treatment of acute or chronic heart failure in man, it is expected that the alkanolamine derivative would be given to man at a total oral dose of between 10 mg. and 200 mg. daily, at doses spaced at 6-8 hourly intervals, or at an intravenous dose of between 1 mg. and 100 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

Sodium bicarbonate (2.5 g.) and then phenyl chloroformate (1.6 g.) are added to a stirred solution of 3-N-(β-aminoethyl)-N-benzylamino-1-(p-benzyloxyphenoxy)-2-propanol (4.06 g.) in toluene (15 ml.), the temperature of the mixture rising to 50° C. Water is added, the mixture is filtered and the solid product is washed with toluene and dried. There is thus obtained 3-N-(β-phenoxycarbonamidoethyl)-N-benzylamino-1-(p-benzyloxyphenoxy)-2-propanol, m.p. 63°-65° C.

A mixture of the above compound (2.63 g.), morpholine (0.48 g.) and toluene (25 ml.) is heated at 100° C. for 72 hours, cooled and diluted with ether. The mixture is washed with aqueous 2N-Sodium hydroxide solution and then with water, dried and evaporated to dryness under reduced pressure. The residue is dissolved in a mixture of ethanol (20 ml.) and acetic acid (20 ml.), a 30% palladium-on-charcoal catalyst (0.1 g.) is added and the mixture is shaken with hydrogen at laboratory temperature and pressure until 250 ml. of hydrogen have been absorbed. The mixture is filtered, the filtrate is evaporated to dryness under reduced pressure and the residue is dissolved in ethanol. An excess of a saturated solution of oxalic acid in ethanol is added, the mixture is filtered and the solid product is washed with boiling ethanol and then dried. There is thus obtained 1-(p-hydroxyphenoxy)-3-β-(morpholinocarbonamido)ethylamino-2-propanol hydrogen oxalate, m.p. 168°-169° C. (with decomposition).

The process described above is repeated except that the appropriate m-benzyloxyphenoxy compound is used in place of the p-benzyloxyphenoxy compound. There is thus obtained 1-(m-hydroxyphenoxy)-3-β-(morpholinocarbonamido) ethylamino-2-propanol hydrogen oxalate, m.p. 122°-126° C.

EXAMPLE 2

The process described in Example 1 is repeated except that the appropriate secondary amine is used in place of morpholine. There are thus obtained the compounds described in the following table:

HO—⟨C₆H₄⟩—OCH₂.CHOH.CH₂NH(CH₂)₂NHCON(R²)(CH₂CH₂OR)

| R | R² | Salt | m.p.(° C.) |
|---|---|---|---|
| H | methyl | hydrochloride dihydrate | (oil) |
| methyl | methyl | hydrogen oxalate | 158–160 |
| H | ethyl | hydrogen oxalate hemihydrate | 149–151 |
| H | β-hydroxyethyl | hydrochloride trihydrate | (oil) |

EXAMPLE 3

A suspension of 1-p-benzyloxyphenoxy-2,3-epoxypropane (11.5 g.) in isopropanol (6ml.) is added to a stirred mixture of 4-(N-β-aminoethylcarbamoyl) morpholine hydrogen sulphate (12.7 g.), potassium hydroxide (7.0 g.) and isopropanol (10 ml.) and the mixture is stirred at 45° C. for 1 hour and then evaporated to dryness under reduced pressure. The residual oil is stirred with water, the mixture is filtered and the solid residue is dissolved in acetone. A 30% w/w solution of hydrogen chloride in propanol is added until the pH of the mixture is less than 2, and the mixture is filtered. The solid residue is crystallised from water and there is thus obtained 1-p-benzyloxyphenoxy-3-(β-morpholinocarbonamidoethyl)amino-2-propanol hydrochloride (4.9 g.).

A solution of the above compound in a mixture of ethanol (20 ml.) and acetic acid (20 ml.) is shaken with a 30% palladium-on-charcoal catalyst (0.1 g.) in an atmosphere of hydrogen at laboratory temperature and pressure until 250 ml. of hydrogen is absorbed. The mixture is filtered, the filtrate is evaporated to dryness under reduced pressure and to the residue is added a hot solution of fumaric acid (1.25 g.) in ethanol (15 ml.). The mixture is kept at 5° C. for 12 hours and is then filtered, and the solid residue is washed with hot ethanol and then dried. There is thus obtained 1-p-hydroxyphenoxy-3-β-(morpholinocarbonamido)ethyl-amino-2-propanol hydrogen fumarate, m.p. 168°-169° C. (with decomposition).

The 4-(N-β-aminoethylcarbamoyl)morpholine hydrogen sulphate used as starting material may be obtained as follows:

Morpholine (4.35 g.) and phenyl chloroformate (6.35 g.) are separately and simultaneously added dropwise during 20 minutes to a stirred mixture of toluene (10 ml.), water (5 ml.) and sodium hydroxide (2 g.) which is maintained at 0° C. The mixture is stirred for a further 2 hours whilst the temperature is allowed to rise to 20° C. The toluene solution is separated, the aqueous solution is extracted twice with toluene (50 ml. each time) and the combined toluene solutions are washed with water, dried and evaporated to dryness under reduced pressure. The residue is crystallised from petroleum ether (b.p. 60°-80° C.) and there is thus obtained N-phenoxycarbonylmorpholine, m.p. 46.5°-47.5° C.

A mixture of the above compound (11 g.) and ethylenediamine (27.8 g.) is stirred at laboratory temperature for 3 days and the excess of ethylene diamine is removed by evaporation under reduced pressure. The residue is dissolved in methanol, the solution is cooled to 5° C. and concentrated sulphuric acid is added until the pH of the solution is 2. A filter-aid ('Celite', 10 g.; 'Celite' is a Trade Mark) is added and the mixture is stirred for 1 hour and then filtered. The filtrate is evaporated to dryness under reduced pressure and the residue is stirred with ethyl acetate. The mixture is filtered and there is thus obtained as solid residue 4-(N-β-aminoethylcarbamoyl)morpholine hydrogen sulphate, m.p. 168°-169° C.

EXAMPLE 4

A mixture of R-(-)-1-p-benzyloxyphenoxy-3-p-toluene-sulphonyloxy-2-propanol (8.56 g.), β-(morpholinocarbonamido)-ethylamine (8.76 g.) isopropanol (40 ml.) and aqueous 2N-sodium hydroxide solution (10 ml.) is heated under reflux for 16 hours, cooled and poured into a mixture of water and ethyl acetate. The organic layer is separated, dried and diluted with petroleum ether (b.p. 60°-80° C.), and the mixture is filtered. The residue is crystallised from a mixture of ethyl acetate and petroleum ether (b.p. 60°-80° C.) and is then purified by chromatography on a silica column (200 g.) using methanol as eluant. There is thus obtained (S)-1-p-benzyloxyphenoxy-3-β-(morpholinocarbonamido)ethylamino-2-propanol. A solution of the above compound (1.2 g.) in acetic acid is shaken with a 30% palladium-on-charcoal catalyst (50 mg.) at laboratory temperature and atmospheric pressure until 90 ml. of hydrogen have been absorbed. The mixture is filtered, the filtrate is evaporated to dryness and the residue is dissolved in ethanol. A molar solution of oxalic acid in ethanol (5 ml.) is added and the mixture is set aside to crystallise. The mixture is filtered and the solid product is recrystallised from a mixture of methanol and ethyl acetate. There is thus obtained S-(-)-1-p-hydroxyphenoxy-3-β-(morpholinocarbonamido) ethylamino-2-propanol hydrogen oxalate, m.p. 150-151° C. $[\alpha]_D^{20}$ = −6.2° (c, 5% in water).

The R-(-)-1-p-benzyloxyphenoxy-3-p-toluenesulphonyloxy-2-propanol used as starting material may be obtained as follows:

A mixture of glycerol 1,2-acetonide (66 g.) and phthalic anhydride (74 g.) is heated at 100° C. for 18 hours and then cooled. The combined syrupy product from three such reactions (415 g.) is dissolved in isopropanol (2.5 liters), (−)-α-methylbenzylamine (148.1 g.) is added and the mixture is kept at laboratory temperature for 4 hours and then filtered. The solid product is crystallised twice from isopropanol (4 liters each time) and there is thus obtained (−)-α-methylbenzylamine o-(2,3-isopropylidenedioxypropoxycarbonyl)benzoate, m.p. 153.5° C.

A solution of the above compound (126.5 g.) in chloroform is shaken with dilute aqueous hydroxchloric acid, and the chloroform layer is separated, washed with water, dried and evaporated to dryness. A mixture of the residue (84.2 g.), water (200 ml.) and aqueous 10N-sodium hydroxide solution (50 ml.) is heated at 100° C. for 10 minutes, cooled and extracted 5 times with ether. The combined ethereal extracts are washed with water, dried and evaporated to dryness, and the residue is distilled under reduced pressure. There is thus obtained (R)-(−)-glycerol 1,2-acetonide, b.p. 84° C./12 mm. Hg, $[\alpha]_D^{20}$ = −9.2° (c, 10% in methanol).

The above compound (32.4 g.) is added to a stirred, cooled mixture of p-toluene-sulphonyl chloride (46.8 g.) in pyridine (25 ml.) and the mixture is stirred for 1 hour and then poured into water. The aqueous mixture is extracted with ether and the extract is washed with water, dried and evaporated to dryness. The residue is crystallised twice from petroleum ether (b.p. 60–80° C.) at −78° C., and there is thus obtained S-(+)-3-p-toluenesulphonylglycerol 1,2-acetonide, $[\alpha]_D^{20}$ = + 3.1° (c, 10% in methanol).

The above compound is converted to R-(−)-1-p-benzyloxyphenoxy-3-p-toluenesulphonyloxy-2-propanol (m.p. 90–91° C., $[\alpha]_D^{20}$ = − 9.1° (c, 20% in ethylacetate) by reaction with p-benzyloxyphenol and hydrolysis of the isopropylidenedioxy group; treatment of the (S)-(+)-3-O-p-benzyloxyphenyl)-glycerol [m.p. 122–123° C., $[\alpha]_D^{20}$ = + 4.3° (c, 4.5% in methanol)] thus obtained with p-toluenesulphonyl chloride; and crystallisation of the product obtained from aqueous isopropanol, by a similar process to that described in the Journal of Medicinal Chemistry, 1973, 16, 168–169 for the preparation of S-(+)-1-(4-acetamidophenoxy)-3-(4-toluenesulphonyloxy)propan-2-ol from R-(−)-α-(4-toluenesulphonyl)acetone glycerol.

What we claim is:

1. An alkanolamine derivative selected from the group consisting of a compound of the formula:

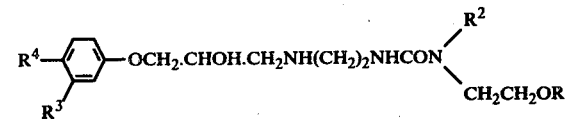

wherein $R^3$ and $R^4$, which may be the same or different, each is hydrogen or hydroxy, provided that at least one of $R^3$ and $R^4$ is hydroxy, and wherein R and $R^2$ are joined together to form ethylene (—CH$_2$CH$_2$—); and non-toxic, pharmaceutically-acceptable acid-addition salts thereof.

2. 1-(p-Hydroxyphenoxy)-3-β-(morpholinocarbonamido)ethylamino-2-propanol or a non-toxic, pharmaceutically-acceptable acid-addition salt thereof.

3. S-(−)-1-(p-hydroxyphenoxy)-3-β-(morpholinocarbonamido)ethylamino-2-propanol or a non-toxic, pharmaceutically-acceptable acid-addition salt thereof.

4. An acid-addition salt as claimed in claim 1, which is a hydrochloride, hydrobromide, phosphate, sulphate, oxalate, fumarate, lactate, tartrate, acetate, salicylate, citrate, benzoate, β-naphthoate, adipate or 1,1-methylene-bis-(2-hydroxy-3-naphthoate), or a salt derived from a sulphonated polystyrene resin.

5. A pharmaceutical composition comprising as active ingredient a cardio selective stimulating amount of at least one alkanolamine derivative or an acid-addition salt thereof, claimed in claim 1, in association with a pharmaceutically-acceptable diluent or carrier therefor.

6. A composition as claimed in claim 5 which is in the form of a tablet, capsule, aqueous or oily solution or suspension , emulsion, injectable aqueous or oily solution or suspension, dispersible powder, spray or aerosol formulation.

7. A composition as claimed in claim 5 which contains, in addition to the alkanolamine derivative, one or more drugs selected from sedatives, vasodilators, diuretics, hypotensive agents, cardiac membrane stabilising agents, agents used in the treatment of Parkinson's disease, cardiotonic agents, α-adrenergic blocking agents and sympathomimetic bronchodilators.

8. A method for the treatment of acute or chronic heart failure in a warm-blooded animal which comprises administering to said animal an effective amount of at least one compound claimed in claim 1.

* * * * *